US012624295B2

(12) United States Patent
Rooney et al.

(10) Patent No.: US 12,624,295 B2
(45) Date of Patent: May 12, 2026

(54) HYDROCARBON PYROLYSIS WITH LESS EXHAUST EMISSION

(71) Applicant: ExxonMobil Chemical Patents Inc., Baytown, TX (US)

(72) Inventors: Mark A. Rooney, Pasadena, TX (US); Thomas T. Hirst, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 837 days.

(21) Appl. No.: 17/782,680

(22) PCT Filed: Dec. 18, 2020

(86) PCT No.: PCT/US2020/066177
§ 371 (c)(1),
(2) Date: Jun. 6, 2022

(87) PCT Pub. No.: WO2021/230917
PCT Pub. Date: Nov. 18, 2021

(65) Prior Publication Data
US 2022/0340822 A1     Oct. 27, 2022

Related U.S. Application Data

(60) Provisional application No. 62/954,783, filed on Dec. 30, 2019.

(30) Foreign Application Priority Data

Apr. 6, 2020     (EP) ..................................... 20168291

(51) Int. Cl.
C10G 9/20     (2006.01)
C07C 4/04     (2006.01)
(Continued)

(52) U.S. Cl.
CPC .................. C10G 9/20 (2013.01); C07C 4/04 (2013.01); C07C 29/106 (2013.01); C07C 29/50 (2013.01)

(58) Field of Classification Search
CPC ......... C07C 4/04; C07C 29/50; C07C 29/106; C07C 9/36; C10G 9/20; C10G 2400/20; F05D 2220/62
See application file for complete search history.

(56) References Cited

U.S. PATENT DOCUMENTS 3,365,387 A     1/1968   Cahn et al.
4,287,377 A     9/1981   Maslin et al.
(Continued)

FOREIGN PATENT DOCUMENTS

EP        0008166 A1     2/1980
JP        2000-204965 A   7/2000
(Continued)

OTHER PUBLICATIONS

Allam power cycle, Wikipedia, Retrieved from URL: <https://en.wikipedia.org/wiki/Allam_power_cycle>, pp. 1-10.
(Continued)

*Primary Examiner* — Jafar F Parsa
(74) *Attorney, Agent, or Firm* — WOMBLE BOND DICKINSON (US) LLP; Kevin Davis

(57) ABSTRACT

Processes, systems, and apparatus are provided for using a common working fluid for one or more turbines for processing a process gas and for the furnace for the pyrolysis process used to produce the process gas. The turbine(s) are operated based on a modified Allam cycle to produce power for operating one or more compressors and/or refrigerators involved in processing of the process gas while producing a reduced or minimized amount of $CO_2$ that is released as a low-pressure gas phase product. Integrating the pyrolysis
(Continued)

furnace with the working fluid loop can provide further benefits.

17 Claims, 4 Drawing Sheets

(51) Int. Cl.
| | |
|---|---|
| *C07C 29/10* | (2006.01) |
| *C07C 29/50* | (2006.01) |

(56) References Cited

U.S. PATENT DOCUMENTS

| | | | |
|---|---|---|---|
| 5,669,216 | A | 9/1997 | Ankersmit et al. |
| 7,815,873 | B2 | 10/2010 | Sankaranarayanan et al. |
| 7,846,401 | B2 | 12/2010 | Hershkowitz et al. |
| 7,943,808 | B2 | 5/2011 | Hershkowitz et al. |
| 8,754,276 | B2 | 6/2014 | Buchanan et al. |
| 8,864,977 | B2 | 10/2014 | Spicer |
| 9,126,882 | B2 | 9/2015 | Lattner et al. |
| 9,187,382 | B2 | 11/2015 | Hershkowitz et al. |
| 9,260,366 | B2 | 2/2016 | Verhaak et al. |
| 9,322,549 | B2 | 4/2016 | Hershkowitz et al. |
| 9,346,728 | B2 | 5/2016 | Keusenkothen et al. |
| 10,190,060 | B2 | 1/2019 | Van Willigenburg |
| 2006/0260321 | A1 | 11/2006 | Minkkinen et al. |
| 2007/0144940 | A1 | 6/2007 | Hershkowitz et al. |
| 2007/0261991 | A1 | 11/2007 | Beattie et al. |
| 2008/0210598 | A1 | 9/2008 | Annamalai et al. |
| 2008/0300438 | A1 | 12/2008 | Keusenkothen et al. |
| 2012/0067056 | A1 | 3/2012 | Palmer et al. |
| 2012/0144837 | A1 | 6/2012 | Rasmussen et al. |
| 2013/0157205 | A1 | 6/2013 | Hershkowitz et al. |
| 2014/0163273 | A1 | 6/2014 | Keusenkothen et al. |
| 2014/0163287 | A1 | 6/2014 | Keusenkothen et al. |
| 2014/0303339 | A1 | 10/2014 | Keusenkothen et al. |
| 2014/0303416 | A1 | 10/2014 | Keusenkothen et al. |
| 2014/0378728 | A1 | 12/2014 | Davis et al. |
| 2015/0166430 | A1 | 6/2015 | Keusenkothen et al. |
| 2015/0197696 | A1 | 7/2015 | Keusenkothen et al. |
| 2016/0176781 | A1 | 6/2016 | Hershkowitz et al. |
| 2017/0058712 | A1 | 3/2017 | Allam et al. |
| 2019/0169510 | A1 | 6/2019 | Pavia et al. |
| 2023/0027105 | A1 | 1/2023 | Rooney et al. |

FOREIGN PATENT DOCUMENTS

| | | |
|---|---|---|
| WO | 2010/077461 A1 | 7/2010 |
| WO | 2021/230917 A3 | 2/2022 |

OTHER PUBLICATIONS

Reliable power for a low-carbon future, Netpower, Retrieved from URL :<https://netpower.com/>, pp. 1-2.

Breaking ground for a groundbreaker: The first Allam Cycle power plant, Modern Power System, Retrieved from URL: <https://www.modernpowersystems.com/features/featurebreaking-ground-for-a-groundbreaker-the-first-allam-cycle-power-plant-4893271/>, 2016, pp. 1-4.

U.S. Appl. No. 62/611,863, "Coke Mitigation In Hydrocarbon Pyrolysis" filed on Dec. 29, 2017, 20 Pages.

U.S. Appl. No. 62/806,274, "Processes and Apparatus for The Removal of Coke and Tar From a Furnace Effluent" filed on Feb. 15, 2015, 15 Pages.

U.S. Appl. No. 62/821,133, "Processes for On-Stream Decoking" filed on Mar. 20, 2019, 14 Pages.

Extended European Search Report received for European Patent Application No. 20168291.1 mailed on Oct. 7, 2020, 11 Pages.

Netl, N., (2010) "Carbon Dioxide Enhanced Oil Recovery Untapped Domestic Energy Supply and Long Term Carbon Storage Solution", National Energy Technology Laboratory, The Energy Lab, Retrieved from the URL :<https://www.netl.doe.gov/sites/default/files/netl-file/co2_eor_primer.pdf>, pp. 1-32.

International Preliminary Report on Patentability received for PCT Application No. PCT/US2020/066177, mailed on Jul. 14, 2022, 12 Pages.

International Search Report and Written Opinion received for PCT Application No. PCT/US2020/066177, mailed on Jan. 21, 2022, 15 Pages.

Allam R. J. , (2013) "NET Power's CO2 cycle: the breakthrough that CCS needs", Modern Power System, Retrieved from URL :<NET Power's CO2 cycle: the breakthrough that CCS needs>, pp. 1-7.

Williamson, K. D., (2019) "Gassing Up", National Review, Retrieved from URL: <https://www.nationalreview.com/2019/03/natural-gas-energy-production-cleaner/>, pp. 1-3.

HYDROCARBON PYROLYSIS WITH LESS EXHAUST EMISSION

CROSS-REFERENCE TO RELATED APPLICATIONS

This application is a US national phase application of PCT Application Serial No. PCT/US2020/066177 having a filing date of Dec. 18, 2020, which claims priority to and the benefit of U.S. Provisional Application No. 62/954,783 having a filing date of Dec. 30, 2019 and European Patent Application No. 20168291.1 having a filing date of Apr. 6, 2020, the disclosures of all of which are incorporated herein by reference in their entireties.

FIELD

The invention relates to lessening exhaust emission from hydrocarbon pyrolysis, to processes for carrying out hydrocarbon pyrolysis with less exhaust emission, to integrated systems for carrying out such processes, to certain exhaust products of the hydrocarbon pyrolysis, and to certain hydrocarbon pyrolysis products.

BACKGROUND

Hydrocarbon pyrolysis processes, e.g., steam cracking, produce commercially-important amounts of useful products and co-products, such as saturated and unsaturated hydrocarbon. Certain pyrolysis products, e.g., $C_{4-}$ olefin, are particularly useful as feedstock for petrochemical processes, e.g., polymerization processes, Pyrolysis processes such as steam cracking use a considerable amount of energy. Since hydrocarbon pyrolysis is highly endothermic, energy is needed to "crack" large hydrocarbon molecules, to produce a pyrolysis effluent comparing molecular hydrogen and desirable hydrocarbon products such as light olefin. The pyrolysis effluent is typically compressed and cooled to facilitate separation and recovery from the pyrolysis effluent of the desired products and co-products, which requires still more energy, e.g., for turbomachinery and refrigeration equipment. When at least apportion of this energy is produced by hydrocarbon combustion, an appreciable amount of exhaust (typically comprising $CO_2$) is emitted, typically as flue gas.

Difficulties have been encountered during attempts to process the exhaust emissions. For example, the high temperatures needed for hydrocarbon pyrolysis (typically at least 700° C.) have been found to limit opportunities to recover and use heat from the combustion exhaust. Alternate approaches to supply the energy through renewable means (e.g. renewable electricity) do not yet have the capacity to supply world demand, let alone the technology solutions to do so.

Therefore, pyrolysis processes such as steam cracking can produce an undesirable amount of exhaust emissions, particularly exhaust emissions containing $CO_2$. Moreover, certain hydrocarbon pyrolysis processes, e.g., steam cracking, produce a pyrolysis effluent that itself contains an appreciable amount of $CO_2$. Attempts have been made to decrease the amount of $CO_2$ and other greenhouse gas ("GHG") emitted by pyrolysis processes and associated combustion processes. Aside from prudent efficiency steps, the only state of the art methods to reduce these emissions have been by using gas treating technology such as an amine treatment to remove $CO_2$ from the combustion exhaust (e.g., from steam cracker furnace flue gas) and from the pyrolysis effluent.

Although this technique is efficient and cost-effective for removing $CO_2$ from the pyrolysis effluent, it is impractical for removing $CO_2$ from combustion exhaust emitted by pyrolysis facilities such as steam cracking facilities. It has been found, for example, that the dilute nature of the exhaust gas (e.g., flue gas) results in the amine treatment corresponding to a sizeable fraction of the overall cost of producing the desired pyrolysis products. There is therefore a need for pyrolysis processes having less exhaust emission, and particularly less $CO_2$ exhaust emission. There is a particular need for steam cracking processes having less $CO_2$ exhaust emission.

Light olefin such as ethylene is typically manufactured in an olefins plant (e.g., a steam cracker plant) which includes production (pyrolysis) facilities and recovery facilities. In certain conventional olefins plants, the olefin production facility includes one or more steam cracker furnaces for steam cracking hydrocarbon-containing feeds. A steam cracker furnace generally includes a convection section and a radiant section. The radiant section includes a plurality of tubular members which are typically referred to as "radiant tubes". Conventionally, the radiant tubes are located proximate to one or more fired heaters, e.g., burners, in the radiant section which heat the outer surface of the furnace tubes. Hot combustion gases exit the radiant section and are introduced into the convection section. The convection section also includes tubular members, typically referred to as "convection tubes". The hot gases from the radiant section heat the outer surfaces of the convection tubes and then exit the convection section.

Conventional steam cracking processes typically produce light olefin by hydrocarbon pyrolysis during pyrolysis mode. Coke and other deposits which form during pyrolysis mode are removed from the furnace internals during regeneration (decoking) mode. During pyrolysis mode, a hydrocarbon-containing feed is introduced into the convection tubes for feed preheating. Feed preheating is carried out in segments of the convection tubes located in an upper region of the convection section. Steam is combined with the preheated feed, and the steam-feed mixture is further heated in segments of the convection tubes located in a lower region of the convection section. The heated feed-steam mixture is introduced into the heated furnace tubes in the radiant section, and heat transferred from the furnace tube to the mixture results in the pyrolysis of at least a portion of the feed to produce a process gas comprising light olefin. During regeneration mode, a flow of oxygenate-containing decoking fluid (e.g., a gaseous steam-air mixture) is substituted for the hydrocarbon-containing feed, and the burners continue to heat the radiant and convection sections. The decoking fluid is conducted through the heated convection tubes, heated radiant tubes, and associated furnace piping, internals, etc., to at least partly remove deposited coke. After sufficient coke removal is achieved, the steam cracking furnace is returned to pyrolysis mode operation.

Further greenhouse gas emissions can be generated due to the need to process the pyrolysis effluent generated during pyrolysis mode operation. For example, separating the desired light olefin components from the remaining components in a pyrolysis effluent can require a plurality of compression and/or refrigeration steps. Each compression and/or refrigeration step represents another process element that requires power, and therefore can represent another location where fuel may be burned to provide such power. While some heat exchange and heat integration may be used to mitigate the amount of additional fuel that is used, it may not be feasible to heat integrate all of the process elements involved in separating desired components from the pyrolysis effluent.

What is needed are systems and methods that can reduce or minimize greenhouse gas emissions when using pyrolysis to produce light olefins, such as when using steam cracking as the pyrolysis method for an ethylene plant.

U.S. Patent Application Publication 2019/0169510 describes systems and methods for decoupling the production and recovery facilities for an olefin plant.

A closed loop cycle sometimes called the "Allam cycle" is described in U.S. Patent Application Publications 2012/0067056 and 2017/0058712 for powering a turbine using $CO_2$ as a working fluid. The Allam cycle is described as provide electric power through natural gas fuel with reduced $CO_2$ emissions.

A modern olefins production plant consumes a large amount of shaft power to drive various compressors and pumps. Energy efficiency improvement in power production for the plant is highly desirable. For example, the process gas compressor discussed in earlier paragraphs can be very large requiring significant amount of shaft power to drive. Additionally, the compressors used in refrigeration units in the olefins production plant can consume large amount of shaft power as well.

From the product recovery section of a typical steam cracker olefins production plant, a large quantity of "tail gas" comprising methane and optionally hydrogen is typically produced. The tail gas is typically combusted as fuel to provide energy, in which process $CO_2$ and water are produced. It would be highly desirable that the energy released from the combustion of the tail gas can be used to power the process steps in the olefins production plant, the $CO_2$ produced can be concentrated, captured, stored, and/or utilized, and the water produced can be used, in an efficient manner There are, however, significant challenges in achieving one, let alone, two or all of these goals.

An olefins production plant including a steam cracker is desirably located close to a user of the olefin products, e.g., polyethylene and/or polypropylene production facilities to minimize the transportation of the olefins. For olefins production plants located close to the source of the hydrocarbon feed and far to the users, it may be highly desirable to convert one or more of the olefin products into a chemical easier to transport in a conversion plant in close proximity to the olefins production plant. It would be highly desirable that the operations of the steam cracker and the recovery section in the olefins production plant, the conversion plant, and a power production plant, if any, including tail gas combustion are integrated to provide a high level of energy efficiency.

This disclosure meets these and other needs.

SUMMARY

The invention is based in part on integration of the effluent processing train for a pyrolysis reactor with the furnace for the pyrolysis reactor to allow a common working fluid to be used. This can allow both a turbine for powering (at least a portion of) the process train and the furnace to be operated based on a modified Allam cycle. The turbine can be used to provide power for the process gas compressor, refrigeration compressors, and/or other portions of the effluent processing train. By powering one or more portions of the effluent processing train using a separate turbine operated based on an Allam cycle, the operation of the processing train can be decoupled from operation of the pyrolysis reactor while also reducing or minimizing emission of $CO_2$ and/or other greenhouse gases. Further $CO_2$ reduction benefits can be obtained by operating the pyrolysis furnace as part of the same working loop.

DETAILED DESCRIPTION

Overview

Figure 1:
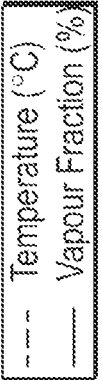
FIG. 1 shows a Mollier diagram for operating a single turbine and a single combustor based on an Allam cycle.

Certain aspects of the invention relate to processes, systems, and apparatus for producing a compressed process gas comprising light olefin such as ethylene. The process utilizes a pyrolysis reactor, e.g., a tubular flow-through reactor, to produce the process gas. A power generator utilizes a turbine operated based on an Allam cycle (using a $CO_2$-containing working fluid) to produce shaft power for operating a compression stage for compressing the process gas while producing a reduced or minimized amount of $CO_2$ that is recovered and conducted away as a gas-phase product. The compression stage compresses the process gas in at least one process gas compressor powered by the produced shaft power. Additionally, at least a portion of the $CO_2$-containing working fluid from the power generation turbine is used as a working fluid for the flow-through reactor environment. By using the $CO_2$-containing working fluid for both the pyrolysis reactor and for one or more of the turbines for providing power for the pyrolysis effluent processing train, production of light olefins can be achieved while reducing, minimizing, or even eliminating exhaust of low-pressure $CO_2$ to the environment.

The $CO_2$-containing working fluid can have a substantially increased $CO_2$ content relative to a conventional working fluid for turbomachinery. Conventionally, air and/or combustion products formed using air as an oxygen source have been used as working fluids. This results in a working fluid where half or more of the working fluid volume corresponds to nitrogen. Instead of using air, a working fluid can be formed from combustion products generated using oxygen from an air separator unit. This can produce a working fluid substantially composed of $CO_2$ and $H_2O$. The $H_2O$ can be separated from the working fluid relatively efficiently, allowing a working fluid with a majority volume of $CO_2$ to be produced.

In order to integrate the pressurized pyrolysis furnace into the same working fluid loop as the combustor and turbine for the process gas compressor, an increased pressure is needed for the working fluid in the reactor shell. Because pyrolysis furnaces are typically operated near ambient pressure (or even at reduced pressure), a variety of structural and process changes are needed to accommodate use of elevated pressure within the pyrolysis furnace. These structural and process changes can include addition of a thicker refractory layer and pressure containing boundary for the furnace reactor wall, including removal of visual inspection windows; modification of the furnace tubes to withstand the elevated pressure; and changes to the methods for coke detection and removal based on the structural changes to the furnace tubes.

In certain aspects, the invention relates to a configuration that can provide the above advantages while integrating the operation of the pyrolysis furnace with other power generation turbines. These aspects can include one or more of the following features, A-F. The invention is not limited to these aspects, and the description of these aspects should not be interpreted as foreclosing other aspects within the broader scope of the invention.

A) A set of turbines that drives not power generation, but instead light olefin unit recovery compression (such as ethylene unit recovery compression). This can include using a set of turbines to drive process gas compression, refrigeration stages, or a combination thereof.

B) A lower pressure outlet for the set of turbines to exhaust a turbine effluent at a temperature 600° C.-700° C. and a pressure of 800 kPa-a or more.

C) A set of one or more low pressure combustors injecting natural gas or tail gas (obtained, e.g., from the steam cracker plant's recovery facility) and oxygen for combustion to heat the turbine effluent from 600° C.-700° C. to 1100° C. In some aspects, a low pressure combustor can use a grid of raw gas burner nozzles and oxygen nozzles to provide combustion heating similar to that demonstrated in heat recovery steam generators as a duct burner. This configuration provides compact heat output for a mixed hot stream used in the reactor vessel.

D) For each low pressure combustor, a close-coupled pyrolysis reactor with hot $CO_2$ on an internally-refractory-lined shell around furnace tubes into which a pyrolysis reactor feed comprising hydrocarbon is introduced and from which a pyrolysis effluent is withdrawn. In some aspects, the reactor can include triangular pitch tubes at a pitch selected to take advantage of the higher radiant efficiency that is provided both from higher pressure operation and from the use of a working fluid that is substantially composed of $CO_2$ and $H_2O$. This can also improve convection heat transfer efficiency. In some aspects, the furnace tubes can correspond to U-tubes to assist within managing thermal expansion with the pressurized reactor vessel. Tube distribution manifolds can be insulated to mitigate external pressure (by providing a lower design temperature for higher allowable stress). In some aspects, process control can be based in part on use of inlet and outlet skin thermowells that are located within the insulated portion of the vessel.

E) Following heat exchange to cool the furnace working fluid exiting from the pyrolysis reactor (with corresponding heating of the working fluid after water removal), the $CO_2$ loop undergoes water knockout and removal, compression to the high pressure side of the loop, and $CO_2$ removal to pipeline. The pyrolysis effluent from the reactor is similarly cooled by heat exchange with pyrolysis feed and by additional dilution steam generation. This approach saves capital and allows for more efficient heat transfer.

F) Decoking of the pyrolysis reactor occurs using steam with a discharge of coke effluent to coke removal facilities upstream of and/or within the quench tower and primary fractionator facilities. The reactor includes erosion-resistant outlet manifolds or channels to manage the erosive impact of decoking. Alternatively, steam and air decoking can be used with consequent need for atmospheric discharge of decoke effluent and more $CO_2$ emissions. To overcome the loss of visual monitoring, inlet and outlet temperature monitoring as well as less severe decoke processes can be used to manage decoke exotherms.

Definitions

The following terms are defined for this description and appended claims.

The term "$C_n$" hydrocarbon means hydrocarbon having n carbon atom(s) per molecule, wherein n is a positive integer. The term "$C_{n+}$" hydrocarbon means hydrocarbon having at least n carbon atom(s) per molecule. The term "$C_{n-}$" hydrocarbon means hydrocarbon having no more than n carbon atom(s) per molecule. The term "hydrocarbon" means a class of compounds containing hydrogen bound to carbon, and encompasses (i) saturated hydrocarbon, (ii) unsaturated hydrocarbon, and (iii) mixtures of hydrocarbons, and including mixtures of hydrocarbon compounds (saturated and/or unsaturated), such as mixtures of hydrocarbon compounds having different values of n.

The terms "alkane" and "paraffinic hydrocarbon" mean substantially-saturated compounds containing hydrogen and carbon only, e.g., those containing ≤1% (molar basis) of unsaturated carbon atoms. The term "unsaturate" and "unsaturated hydrocarbon" refer to one or more $C_{2+}$ hydrocarbon compounds which contain at least one carbon atom directly bound to another carbon atom by a double or triple bond. The term "olefin" refers to one or more unsaturated hydrocarbon compound containing at least one carbon atom directly bound to another carbon atom by a double bond. In other words, an olefin is a compound which contains at least one pair of carbon atoms, where the first and second carbon atoms of the pair are directly linked by a double bond. The term "aromatics" and "aromatic hydrocarbon" mean hydrocarbon compounds containing at least one aromatic ring.

The term "pyrolysis" means an on-average endothermic reaction for converting molecules into (i) atoms and/or (ii) molecules of lesser molecular weight, and optionally (iii) molecules of greater molecular weight, e.g., processes for converting ethane and/or propane to molecular hydrogen and unsaturates such as ethylene, propylene and acetylene.

The term "Periodic Table" means the Periodic Chart of the Elements appearing on the inside cover of The Merck Index, Twelfth Edition, Merck & Co., Inc., 1996. "Steam Tables" can be found in M. D. Koretsky, "Engineering and Chemical Thermodynamics", John Wiley & Sons, 2004. When a temperature is indicated, the units "K" indicate degrees Kelvin, the SI unit of temperature.

Operating a Pyrolysis (Steam Cracking) Furnace at Elevated Pressure

Steam cracking is an example of a pyrolysis process where heat is transferred indirectly into the pyrolysis environment through the walls of a furnace tube (or another type of vessel). This has the advantage of keeping the desired pyrolysis products segregated from the combustion and/or heating environment. However, this also means that any coke formed during pyrolysis is also segregated, and therefore is not consumed or transported away by the processing environment. Thus, monitoring of coke build-up is required, along with periodic removal of the accumulated coke.

Conventionally, the containment vessel for the heating environment surrounding the furnace tubes is operated at relatively low pressures, such as pressures of 150 kPa-a or less. This is based on a variety of considerations. First, operating the containment vessel/heating environment at relatively low pressure avoids the need to perform substantial compression of air, which is the typical oxygen source and working fluid for a conventional steam cracking furnace. It is noted that the use of air means that the working fluid in a conventional steam cracking furnace contains a substantial amount of nitrogen. Second, due to coke accumulation with the reactor tubes of a steam cracker, visual inspection is typically used to identify coke build-up during pyrolysis within the reactor tubes. Visual identification can also assist with avoiding undesired hot spots during coke removal. Conventionally, such visual inspection windows are not structurally suitable for inclusion in reactor tubes when the heating environment is operated at a pressure of 150 kPa-a or more.

Operating a steam cracking furnace environment with low pressure air as the oxygen source also means that a substantial quantity of low pressure, dilute $CO_2$ is created. Historically, a substantial portion of the low pressure, dilute $CO_2$ from steam crackers has been exhausted to the atmosphere. One option for capturing this low pressure, dilute $CO_2$ is to treat the furnace effluent with an amine wash. However, this requires substantial additional cost, due to the large volume of low pressure gas that is generated by the furnace.

In contrast to conventional operation, in various aspects, a pressurized steam cracker vessel (or other pressurized vessel for a pyrolysis environment) and one or more associated turbines can be operated to have at least a portion of the working fluid in common. For example, one or more pressurized vessels for pyrolysis and one or more turbines for associated process gas compressor(s) can be operated based on an Allam cycle using a $CO_2$-containing fluid as a common working fluid. By using a common working fluid, the creation of large volumes of low pressure, dilute $CO_2$ is avoided. Instead, high purity, high pressure $CO_2$ can be withdrawn from the system during operation. This high purity, high pressure $CO_2$ can be directly used as a reagent or for sequester. Alternatively, the high purity, high pressure $CO_2$ may require a reduced or minimized amount of further processing to be suitable for use as a reagent or for sequester.

To integrate the working fluid for both a turbine combustor and a pressurized pyrolysis environment, the turbine combustor is operated at relatively high pressure, such as a pressure of 15 MPa-a or more, or 20 MPa-a or more. After powering the turbine, the working fluid is at a reduced pressure. The reduced pressure working fluid is then passed into a low pressure combustor to re-heat the turbine effluent from roughly 700° C. to 1100° C. This combustion can then be close coupled with the pressurized vessel to provide high-temperature pyrolysis heat transfer. The pressurized vessel for the pyrolysis environment can operate at a pressure of 800 kPa-a or more, or 1000 kPa-a or more. Depending on the aspect, the combined concentration of $CO_2$ and $H_2O$ can correspond to 80 vol. % or more of the fluid in the pressurized vessel for the pyrolysis environment, or 90 vol. % or more, or 95 vol. % or more, such as up to containing substantially only $CO_2$ and $H_2O$ (less than 1.0 vol. % of other components). This is in contrast to conventional steam cracker furnace operation at roughly 100 kPa-a and a combined concentration of $CO_2$ and $H_2O$ of roughly 30 vol. %. It is noted that using a working fluid composed primarily of $CO_2$ and $H_2O$ can provide an improved radiative efficiency per unit flue gas volume, resulting in significant footprint and capital savings. In some aspects, still higher pressures can be used in the pressurized vessel for the pyrolysis environment, such as a pressure of 1300 kPa-a or more, or 1500 kPa-a or more, or 2000 kPa-a or more, such as up to 3000 kPa-a or possibly still higher. Such higher pressures can be used to improve cycle efficiency and reduce reactor plot/surface area with suitable mechanical design.

In addition to having improved radiative efficiency, the increased pressure within the high pressure steam cracker furnace can allow for increased convective heat transfer. This can allow, for example, improved convective heat transfer per available surface area, thus reducing the amount of high-alloy heat transfer area that is required to provide a desired level of heat transfer to the process gas within the reactor tubes. This allows for still additional capital cost savings.

Ancillary low-temperature heating steps can be provided with waste heat recovery from quench systems or the $CO_2$ loop. Ancillary low-temperature cooling steps can be provided using dilution steam condensate preheat or air fin heat exchangers. With this approach, requiring no furnace stacks, no boiler stacks, no cooling towers, and no decoke vents, emissions to the atmosphere are virtually eliminated.

Process Cycle Overview

FIG. 1 shows an example of a Mollier diagram (pressure versus enthalpy plot) for a single combustor and a turbine operating based on an Allam cycle. FIG. 1 also shows lines corresponding to constant temperature curves (Temperature in ° C. is indicated on the upper long axis of the figure), as well as the region of phase space where distinct vapor and liquid phases of $CO_2$ can be present when $CO_2$ is not in a supercritical state. In the Example shown in FIG. 1, the working fluid loop only includes the combustor and associated turbine. In other words, the turbine and the pyrolysis furnace are not integrated in the cycle shown in FIG. 1.

In FIG. 1, the Allam cycle is illustrated based on how various processes within the cycle result in pressure and/or enthalpy changes for the working fluid. The cycle can begin with addition of fuel input 610 to the working fluid before passing the fuel and working fluid into the combustor. The fuel is combusted (completed at 620), which results in an increase in enthalpy at relatively constant pressure. This high pressure, high enthalpy working fluid is then used to power a turbine 630. Powering the turbine 630 results in a reduction in both pressure and enthalpy for the working fluid. The depressurized working fluid is then heat exchanged 640 with the high pressure working fluid 680 that the fuel input 610 is combined with. The heat exchange reduces the enthalpy of the low pressure working fluid while increasing the enthalpy of the high pressure working fluid.

After heat exchange, water is removed 650 from the working fluid. The water removal is performed by cooling the working fluid to condense the water. However, such cooling has the potential to also place the working fluid in a region of phase space where the $CO_2$ in the working fluid would no longer be supercritical. To avoid this, as shown in FIG. 1, the water removal 650 is performed in a series of alternating cooling steps 652 and compression steps 654. This allows the $CO_2$ in the working fluid to remain (substantially) in a supercritical state during the water removal process, so that no phase changes occur in the working fluid. After water removal 650, the remaining working fluid substantially corresponds to $CO_2$. The $CO_2$ working fluid is then further compressed (e.g., by pumping) 660 to return the working fluid to the desired pressure for the combustor 620. After pressurization 660, the working fluid is then heated 670 and heat exchanged 680 in preparation for the combustor.

Figure 2:
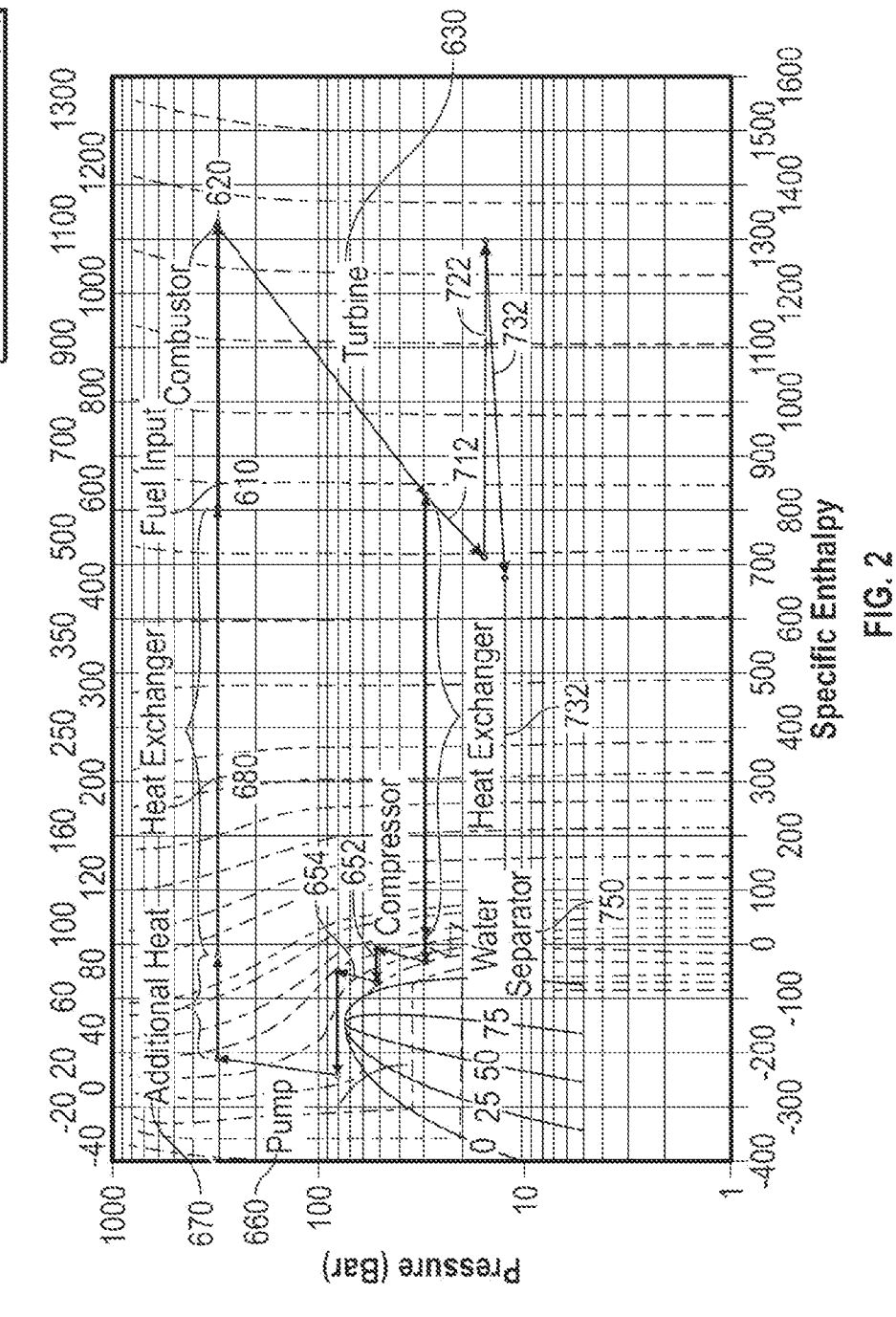
FIG. 2 shows a Mollier diagram for integration of a pyrolysis furnace (combustor and reactor housing) with a combustor and turbine.

FIG. 2 shows another example of a Mollier diagram (pressure versus enthalpy plot). In FIG. 2, the Mollier diagram shows a process cycle where a combustor, a turbine, and a pyrolysis furnace are operated based on an Allam cycle. FIG. 2 also shows lines corresponding to constant temperature curves (in ° C. per upper long axis), as well as the region of phase space where distinct vapor and liquid phases of $CO_2$ can be present due to $CO_2$ not being in a supercritical state.

In FIG. 2, the portions of the cycle that are similar to FIG. 1 are designated by a similar numeral. The cycle begins with addition of fuel input 610 to the working fluid prior to passing the fuel and working fluid into the combustor. The fuel is combusted 620, which results in an increase in enthalpy at relatively constant pressure. This high pressure, high enthalpy working fluid is then used to power a turbine 630. Powering the turbine 630 results in a reduction in both pressure and enthalpy for the working fluid.

Unlike the cycle shown in FIG. 1, the depressurized working fluid exiting the turbine 630 is not heat exchanged. Instead, in the cycle shown in FIG. 2, additional fuel 712 is added to the turbine effluent. The combined additional fuel and turbine effluent is then combusted 722 in one or more low pressure combustors to produce a working fluid with increased enthalpy. The increased enthalpy working fluid provides heat 732 for the pyrolysis furnace. After exiting from the furnace, the furnace effluent is heat exchanged 742 with the high pressure working fluid 680 that the fuel input 610 is combined with. The heat exchange reduces the enthalpy the enthalpy of the low pressure working fluid while increasing the enthalpy of the high pressure working fluid.

After heat exchange, water is removed 750 from the working fluid. Due to the additional low pressure combustion 722 and provision of heat 732 for the pyrolysis furnace, the working fluid is at a lower pressure prior to water removal relative to the process in FIG. 1. Thus, additional cycles of cooling and compression may be needed to remove water while maintaining the $CO_2$ in the working fluid in a single (supercritical) phase. After water removal 750, the remaining working fluid substantially corresponds to $CO_2$. The $CO_2$ working fluid is then further compressed 660 to return the working fluid to the desired pressure for the combustor 620. After pressurization 660, the working fluid is then heated 670 and heat exchanged 680 in preparation for the combustor.

The composition of the working fluid can vary, depending on the location in the cycle where the working fluid is sampled. After combustion and prior to removal of water, the working fluid can include $CO_2$, $CO$, $H_2O$, and optionally one or more components that are present due to the fuel containing compounds other than hydrogen and hydrocarbons and/or due to use of an oxygen-containing stream that contains compounds other than oxygen. Optionally but preferably, the oxygen-containing stream can include 90 vol. % or more of $O_2$, or 95 vol. % or more, or 97 vol. % or more, such as having an oxygen-containing stream that is substantially composed of $O_2$ (less than 0.1 vol. % of components different from 02). Optionally but preferably, the fuel used for combustion can include 90 vol. % or more of hydrogen, hydrocarbons, $CO$, $CO_2$, and $H_2O$, or 95 vol. % or more, or 97 vol. % or more, such as up to containing 0.1 vol. % or less of other components. Suitable fuels include those specified for pyrolysis reactor regeneration, e.g., a fuel having a heating value$\geq 1 \times 10^6$ J/kg. For example, the fuel can comprise one or more of natural gas, gaseous hydrocarbon in the natural gas, gaseous hydrocarbon separated from the natural gas and/or derived from the natural gas, gaseous hydrocarbon separated from the natural gas condensate and/or derived from the natural gas condensate, gaseous hydrocarbon separated from the crude oil and/or derived from the crude oil, molecular hydrogen, carbon monoxide, and mixtures thereof. Additionally or alternately, a tail gas stream generated from the ethylene plant can be used as at least a portion of the fuel.

After water separation and prior to addition of more fuel, the working fluid can include less than 1.0 vol. % water, or less than 0.1 vol. % water. Additionally or alternately, the working fluid after water separation and prior to addition of more fuel can include 90 vol. % or more of $CO_2$, or 95 vol. % or more, or 97 vol. % or more, such as up being substantially composed of $CO_2$ (less than 1.0 vol. % of components different from $CO_2$, or less than 0.1 vol. %.)

The tail gas recovered from the process gas can consist essentially of methane and optionally hydrogen at various concentrations. The tail gas stream from a large industrial steam cracker receiving feeds such as ethane can be quite large. In an embodiment of the processes of this disclosure, a portion, and preferably a majority, and preferably the entirety, of the tail gas is combusted in the Allam cycle to produce power, including shaft power and optionally electrical power via coupled electricity generator(s). The shaft power can be advantageously used to drive one or more of the equipment in the olefins production plant, e.g.: a) to a process gas compressor to compress the process gas, b) to a refrigeration compressor to cool the compressed process gas, c) to a refrigeration compressor to cool the decompressed working fluid in a cooling step from the series of cooling and compressing steps, or d) a combination of two or more of a), b) and c). Compared to using power sourced from external fuel such as a natural gas stream, or electrical power transmitted from outside of the olefins production plant, using the shaft power produced from tail gas combustion in an Allam cycle can improve the energy efficiency of the olefins production plant significantly. Electrical power can be co-generated in the olefins production plant by coupling a portion of the shaft power to one or more electricity generators to suit the electricity demand in the olefins plant, and to transmit to outside of the plant where appropriate and economic. The in-situ generated electrical power, when consumed on-site, does not involve transmission loss otherwise unavoidable if it were transmitted from a remote power plant. An olefins production plant consumes a large quantity of shaft power, which can be met by using a large scale Allam cycle achieving a very high level of economy of scale. In contrast, the power production units disclosed in U.S. Patent Application Publication No. 2017/0058712 A1 are at much smaller in scale and therefore less efficient.

In a conventional Brayton cycle such as one disclosed in U.S. Patent Application Publication No. 2019/0169510 A1, the exhaust gas comprising $CO_2$ and water produced from fuel combustion is typically vented into the atmosphere, resulting in large $CO_2$ emission and loss of water vapor. On the contrary, any water produced in the Allam cycle of the processes of this disclosure can be advantageously reused. For example, at least a portion of a water stream can be (i) fed into the pyrolysing step to mix with the hydrocarbon-containing feed; (ii) heated to generate steam; (iii) used as an indirect cooling medium; (iv) used as a quenching medium; and (iv) fed into a hydrocarbon-containing stream as a diluent. An olefins production plant utilizes a lot of water for cooling and as process diluent. The Allam cycle used in the processes of this disclosure in an olefins production plant can produce very large quantity (e.g., 1500 kilotons per year for a state-of-art olefins production plant) of water due to the amount of fuel combusted. By reusing the water stream produced from the Allam cycle, demand of externally-sourced water is reduced in the plant, further increasing the plant efficiency, reducing the plant carbon footprint, and improving the environmental friendliness thereof.

An olefin product produced from an olefins production plant can be an ethylene stream. The ethylene product can find many industrial uses. For example, the ethylene stream can be supplied via a pipeline to a nearby polyethylene production plant where it is converted into polyethylene. In another embodiment, a portion of the ethylene product can be converted into glycol products including but not limited to monoethylene glycol ("MEG"), which, in turn, can be used in vehicle antifreeze and in processes for making polyester polymers. In a particularly advantageous process, ethylene can be first oxidized by oxygen to produce an oxidized mixture comprising ethylene oxide, which can subsequently hydrolyze to make MEG, or contact $CO_2$ to produce ethylene carbonate followed by hydrolysis to make MEG:

$$\text{Ethylene} + O_2 \rightarrow \text{Ethylene oxide} \tag{1}$$

$$\text{Ethylene oxide} + H_2O \rightarrow \text{MEG} \tag{2}$$

$$\text{Ethylene oxide} + CO_2 \rightarrow \text{Ethylene carbonate } (C_3H_4O_3) \tag{3}$$

$$\text{Ethylene carbonate} + H_2O \rightarrow \text{MEG} + CO_2 \tag{4}$$

The oxygen consumed in reaction (1) above can be supplied by an air separation facility which also supplies the oxygen-containing stream required for combusting the fuel such as the tail gas in the Allam cycle. By using a common air separation facility for two processes, which is costly, one can achieve an economy of scale otherwise not possible, resulting in a high energy efficiency and cost effectiveness among all involved plants.

The $CO_2$-containing stream and/or the compressed $CO_2$ stream produced from the Allam cycle in the processes of this disclosure can be put into advantaged use in various embodiments. For example, a portion of the $CO_2$ produced in the Allam cycle can be supplied to reaction (4) in the preceding paragraph, enabling the efficient production of MEG from the ethylene produced from the ethylene production plant. In another example, a portion of the compressed $CO_2$ stream can be used to extract a hydrocarbon source material, which, in turn, can be used to derive at least a portion of the hydrocarbon-containing feed subjected to pyrolysis to make the olefins products. Such hydrocarbon source material can be, e.g., crude oil, shale oil, shale gas, natural gas, and the like, stored in underground geological formations. From the extracted crude oil, shale oil, shale gas, and/or natural gas, one can derive a suitable feed, e.g., a natural gas stream, an ethane stream, and the like, as feed to the steam cracker in an olefins production plant. The integration of the Allam cycle, olefins production, and hydrocarbon extraction in such manner can greatly facilitate the overall production processes, and substantially increase the overall energy efficiency. Any surplus $CO_2$ produced from the Allam cycle can be conveniently injected into underground storages for sequestration, which are frequently available at hydrocarbon extraction sites. Alternatively or additionally, a portion of the compressed $CO_2$ stream can be conveniently supplied via a pipeline to other locations for sale, storage, or use. Overall, the olefins production processes of this disclosure can leave a very small $CO_2$ footprint, in stark contrast to a conventional process which can produce large quantity of $CO_2$.

By combusting the large quantity tail gas produced in the olefins production plant in the Allam cycle in the processes of this disclosure, one therefore can conveniently dispose of a relatively low value fuel stream, produce large and flexible quantities of shaft power and/or electrical power as needed by the olefins production plant, supply a large quantity of process water otherwise required from external source to the olefins production plant, supply oxygen to adjacent processes such as MEG production processes at higher economy of scale, and facilitate hydrocarbon extraction using the $CO_2$ stream, all with a minimized $CO_2$ emission and water emission. The total benefit of the processes of this disclosure can be enormous.

Configuration Example

Figure 3:
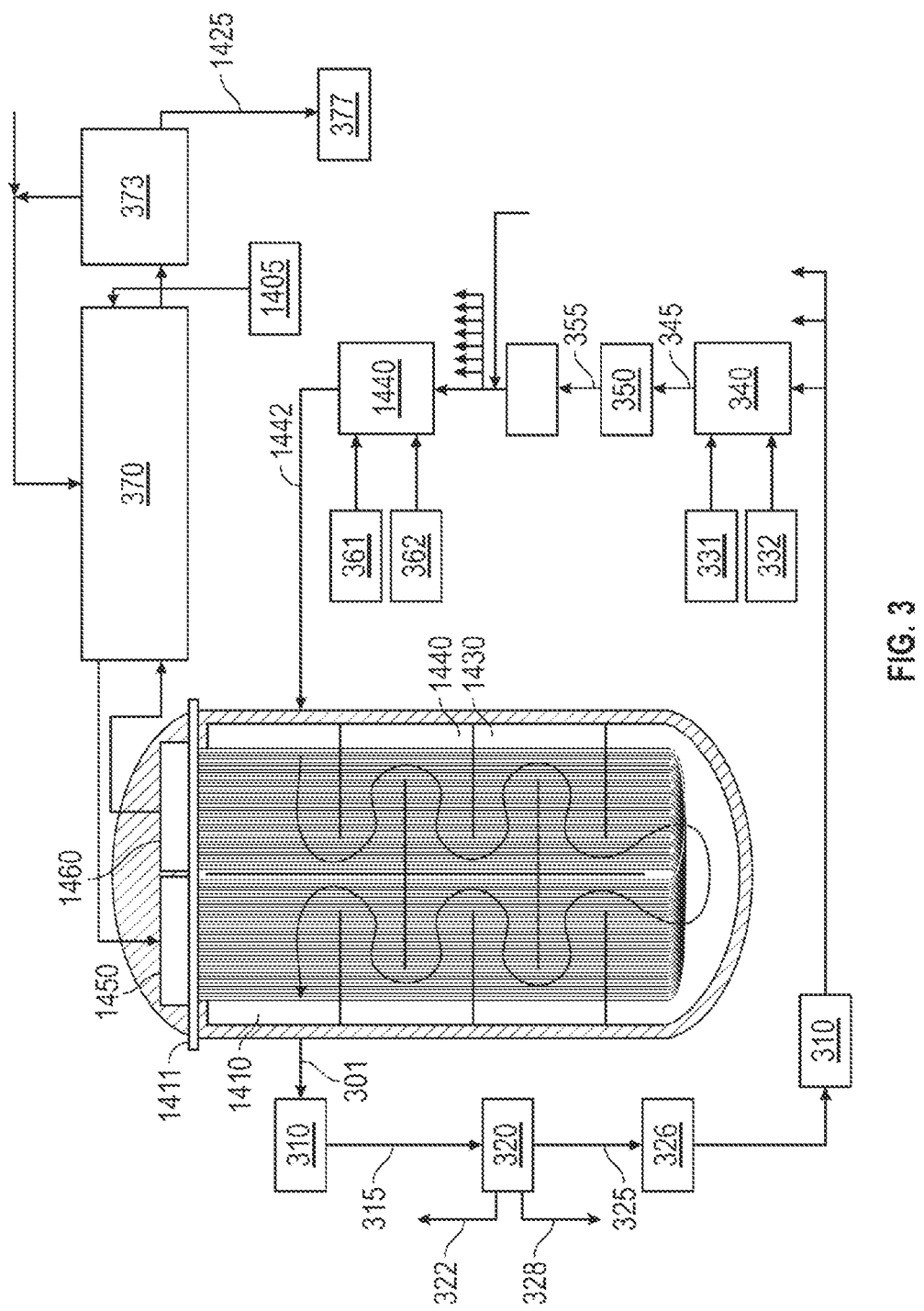
FIG. 3 shows an example of a pyrolysis reactor configuration that is suitable for integration with a combustor and associated turbine.

FIG. 3 shows an example of a configuration for integrating the working fluid for a pyrolysis furnace with the working fluid for a combustion turbine. In FIG. 3, a pyrolysis reactor shell 1411 that defines a reactor volume 1410 and corresponding reactor tubes or furnace tubes 1420 within the reactor volume 1410 are shown. The furnace tubes 1420 in FIG. 3 correspond to U-shaped tubes, although other convenient furnace tube shapes could be used. Several internal baffles 1430 are also illustrated. The internal baffles 1430 can lengthen the path of the working fluid within the reactor volume 1410 while keeping the working fluid substantially in contact with the furnace tubes 1420. During operation, heated working fluid 1442 that was heated to a desired temperature for the pyrolysis environment by combustion in a low-pressure combustor 1440 is passed into reactor volume 1410. The heated working fluid 1442 flows through reactor volume 1410 along the path defined by baffles 1430. The extended path length created by baffles 1430 assists with transfer of heat from heated working fluid 1442 to reactor tubes 1420. A pyrolysis feed (and any optional diluent steam) 1405 is passed into an inlet manifold 1450 that distributes the pyrolysis feed 1405 into the various furnace tubes 1420. The pyrolysis feed 1405 reaches pyrolysis temperature within the reactor tubes to form pyrolysis effluent 1425. Pyrolysis effluent 1425 exits from furnace tubes 1420 via outlet manifold 1460. The pyrolysis feed 1405 is heated prior to entering furnace tubes 1420 by heat exchange 370 with pyrolysis effluent 1425. The heat exchanged pyrolysis effluent 1435 can then be further heat exchanged 373 to form steam, which can be used as a diluent for the pyrolysis feed 1405. The cooled pyrolysis effluent can then be passed into the start of the recovery system 377 for processing the pyrolysis effluent to recover desired products.

After transferring heat to the furnace tubes 1420, the furnace exhaust gas 301 can exit from reactor volume 1410. The furnace exhaust gas is passed into a heat exchanger 310 to further cool the furnace exhaust gas. The cooled furnace exhaust gas 315 is then cooled and compressed in a series of steps 320 to remove water 322 from the remaining working fluid 325. A portion of the working fluid, now composed of substantially $CO_2$, can also be withdrawn 328 after removing water 322. The working fluid 325 is then optionally heated 326 prior to entering heat exchanger 310 to further raise the temperature of working fluid 325. The heated working fluid 325 is then combined with fuel 331 and oxygen 332 prior to being passed into combustor 340. The fuel 331 and oxygen 332 are combusted in the presence of working fluid 325 to form a heated working fluid 345. The heated working fluid 345 is used to drive one or more turbines 350 to produce shaft power and/or electricity for use by various compressors and/or refrigeration units 353. The depressurized working fluid 355 is combined with additional fuel 361 and oxygen 362 for combustion in low-pressure combustor 1440.

Figure 4:
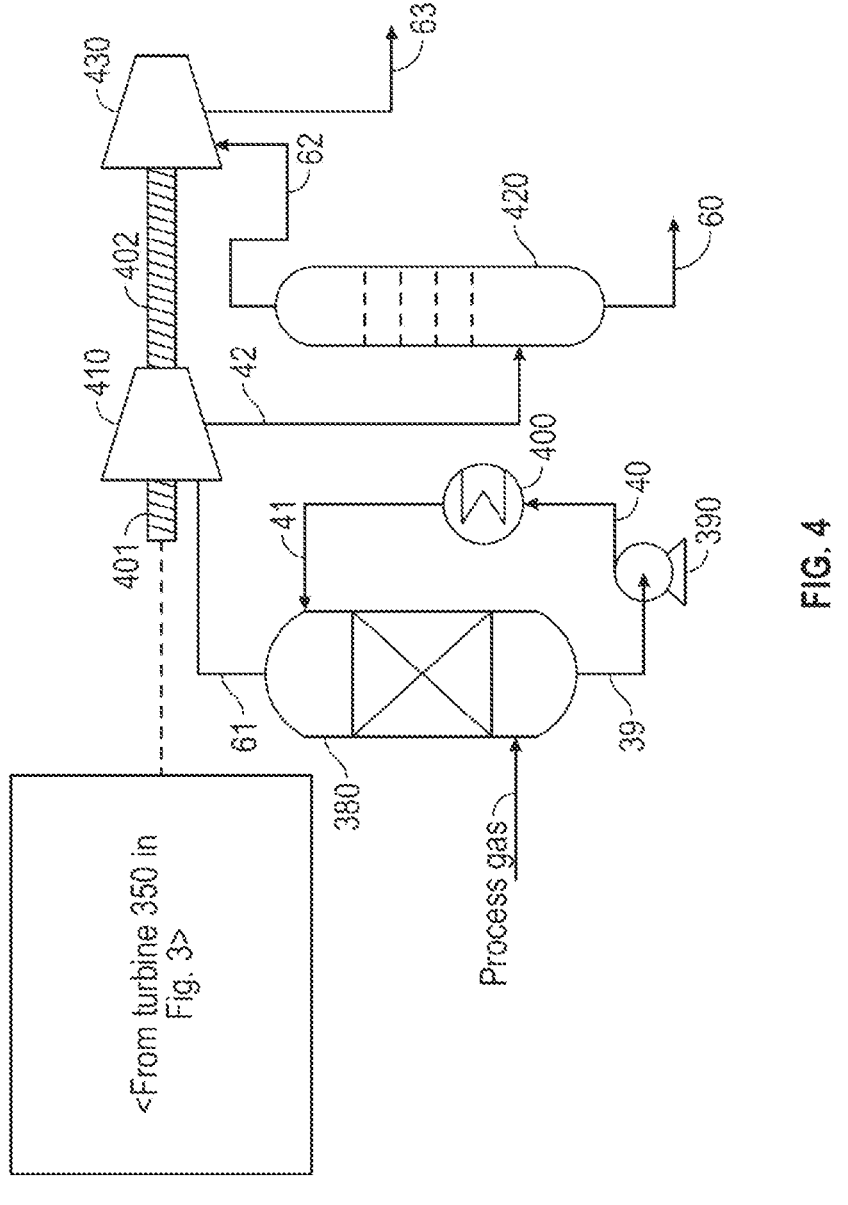
FIG. 4 schematically shows certain aspects of the invention in which a process gas produced derived from hydrocarbon pyrolysis product is compressed in a process gas compressor.

FIG. 4 shows an example of how power provided by a turbine can be utilized to power a process gas compressor. An example of a suitable power plant is shown schematically in FIG. 4. In FIG. 4, process gas (e.g., from line 49 of FIGS. 1 and 2) is conducted to cooling stage 380 (typically a quench tower or combined quench tower-primary fractionator) to produce a cooled process gas, which is conducted away via line 61. Water is a typical quench medium, which can be recovered via line 39, pressurized in pump 390, conducted to cooler 400 via line 40, and returned to the cooling stage via line 41. Cooled process gas is initially pressurized in compressor stages 410, which typically include at least three stages of increasing compression and inter-stage cooling. Pressurized process gas from the compressor stages 410 is conducted via line 42 to process gas upgrading equipment, typically caustic and/or amine treatment, shown schematically as tower 420. Spent treatment medium (e.g., spent caustic) is conducted away via line 60. Upgraded process gas is conducted via line 62 to second compression stages 430 for further pressurization. Typically, stages 410 and 430 are joined by rotating shaft 402, which may be joined to rotating shaft 401 for powering these stages. Shaft 402 obtains at least a portion of its shaft power from turbine 520 (as shown in FIG. 5). This can be accomplished by (i) a direct transfer of rotational energy, e.g., via a rotational power transmission; (ii) an indirect transfer, e.g., by powering an electric generator with power 599 from turbine 520, driving an electric motor with at least a portion of the electric power produced by the generator, and using the motor to power shaft 401; and (iii) a combination of direct and indirect power transmission. Compressed process gas is conducted away via line 63 for storage and/or further processing, e.g., drying, acetylene conversion, and recovery of products such as ethylene.

In FIG. 3 and FIG. 4, process elements can be described as being in fluid communication, meaning that fluids can be passed from one process element to another. Fluid communication includes direct fluid communication and indirect fluid communication. For example, in FIG. 4, cooling stage 380 is in direct fluid communication with compressor stage 410, as fluid can flow between cooling stage 380 and compressor stage 410 without passing through an intervening process element. Cooling stage 380 is in indirect fluid communication with tower 420 via compressor stage 410. It is noted that in FIG. 3, furnace tubes 1420 are not in fluid communication with reactor volume 1410.

Additional Modifications of Furnace Tubes and Pressurized Pyrolysis Vessel

Operating a pyrolysis environment at an elevated pressure (such as 800 kPa-a or more) presents a variety of additional challenges. These challenges can include providing a suitable pressurized vessel to contain the pyrolysis environment and exposing the furnace tubes to an elevated external pressure at high temperature. Additionally, the pyrolysis reaction within the tubes can be managed to reduce coking, but tube mechanical design and external pressure are also balanced to mitigate the effects of creep of tubes under external pressure.

With regard to providing a suitable pressurized vessel for containing the pyrolysis environment, a sufficient thickness of refractory material can be added to the pressure-retaining shell to allow the furnace to maintain structural stability. Having sufficient pressure containment can correspond to providing sufficient containment for a fluid at a pressure of 800 kPa-a to 3000 kPa-a and a temperature of 1000° C. or more, or 1100° C. or more, such as up to 1400° C. or possibly still higher. These conditions present mechanical design challenges for both the reactor shell and the furnace tubes. To provide sufficient pressure containment with practical materials and thicknesses, the internal wall of the pressurized vessel can include a roughly 300 mm (or thicker) internal refractory material consistent with a pyrolysis furnace. This internal refractory material can sufficiently insulate the wall to allow for nearly ambient temperature wall mechanical design. This can allow, for example, carbon steel or low Cr steel wall construction.

It is noted that the working fluid in the pressurized vessel contains both $H_2O$ and $CO_2$, as water removal in the process cycle does not occur until after the working fluid exits the pyrolysis environment. Although the $CO_2$ is maintained in a supercritical state, the water can potentially be in either a vapor or liquid phase. Thus, if the pyrolysis environment was allowed to drop to a sufficiently low temperature, the possibility would exist of forming corrosive $CO_2$-rich water condensation on the back side of the refractory material. To counteract this, a higher design temperature (and higher minimum operating temperature) of can be used for the inside reactor wall, such as a temperature between 160° C. to 400° C. Overall, this results in a shell mechanical design well within the capability of commercially available materials and thicknesses.

The capacity per pyrolysis reactor is selected to provide a practical shell diameter as well as a prudently-sized portion of the steam cracking plant flow to allow for maintenance of one reactor (as in for cracking tube replacement) without affecting overall steam cracker throughput. Based on typical configuration with pyrolysis furnaces, this results in about 7-8 reactors with 250-300 kTA (thousands of tons per year) of ethylene capacity per reactor for a world-scale 1800 kTA unit based on ethane. An example of a reactor having this capacity can be a reactor that contains approximately 160 U-tubes. Based on tube pitch required from mean beam length calculations, this results in 3-4.5 m diameter per reactor, as measured outside of the refractory.

In addition to maintaining structural stability, using a pressurized vessel for the pyrolysis environment presents various other challenges. For example, any locations where the furnace tubes penetrate into the pressurized vessel need to account for thermal expansion and contraction. An example of a suitable tube configuration that can account for thermal expansion and contraction is a "U-tube" type arrangement.

More generally, it can be desirable to reduce or minimize the number of distinct locations where a flow path for the pyrolysis feed and/or product crosses into or out of the pressurized vessel. One option for reducing or minimizing the number of interfaces between the pyrolysis feed/product flow path and the pressurized vessel is based on using manifolds. Manifolds for splitting the pyrolysis feed into individual reactor tubes can be located inside the pressurized vessel. To manage external pressure on these larger manifolds with readily available materials and practical thicknesses, the manifolds can be located inside an internally-insulated portion of the pressurized hot side vessel. Alternatively, refractory-lined tubesheets can split the pyrolysis feed from inlet channels into individual reactor tubes and/or can re-join the pyrolysis effluent into one or a reduced number of conduits at the reactor outlet. When using such options, individual tube inlets can be equipped with nozzles, restriction orifices, or venturis to improve distribution of flow among tubes from a given manifold or distributor. These nozzles, orifices, or venturis provide the pressure difference used to generate a temperature difference to facilitate monitoring of coke accumulation.

Tube size and thickness can be selected accommodate the heat transfer and hydraulic impediment of internal coking. In one embodiment, alumina former tubes can be used to reduce coking and allow for less coke for lower temperature tubes or smaller diameter tubes or both. This approach could facilitate higher external mechanical design pressure for improved cycle efficiency and reduced heat transfer/plot area. Similarly, the internal diameter of the tubes can be selected to reduce or minimize pressure drop as coke accumulates in the furnace tubes. If desired, small fins can be added to the tubes for stiffening (or for slightly improved heat transfer) to allow somewhat higher hot side operating pressure.

The increased pressure in the pyrolysis reactor vessel creates some processing challenges as well. For instance, high temperature operation in steam cracking results in internal coking which must be monitored and decoked periodically. With a pressurized vessel operating at a pressure of 800 kPa-a or more, sufficient means for monitoring need to be provided without reliance on visual inspection. U.S. provisional patent application 62/611,863 details a measurement technique for monitoring coke buildup among adjacent radiant tubes. The technique is based on a relationship between the pressure and temperature across an adiabatic transition (such as a nozzle). This inlet temperature monitoring combined with outlet temperature monitoring and inlet pressure monitoring can provide the required surveillance of radiant tube coking (as well as decoking) as described in U.S. provisional patent application 62/611,863. This temperature monitoring also enables coil leak detection as a high temperature would indicate leakage of high-pressure hot $CO_2$ into the reactor tubes.

Further, typical industry use of decoking with steam and air results in exotherms that are monitored through visual inspection of the outside of the tubes in order to avoid damage due to hot spots within the tubes. Without visual inspection capability to monitor for hot spots, a method of coke removal can be used that removes coke without these exotherms. U.S. Pat. Nos. 3,365,387 and 8,864,977 provide examples of methods for endothermic coke removal without air. For example, U.S. Pat. No. 8,864,977 describes methods for removing coke by stopping the flow of process gas in the furnace tubes, introducing steam (or another removal fluid) into the furnace tubes, and maintaining the furnace tubes below 780° C. while coke is removed. As another example, U.S. provisional patent application 62/821,133 details processes and controls to use steam at sufficiently high pressure to perform endothermic removal of coke from steam cracking furnaces with no atmospheric emission of decoking effluent. As still another example, U.S. provisional patent application 62/806,274 details knockout facilities that can be used to remove coke and tar from pyrolysis effluent to facilitate decoking without atmospheric emissions of decoking effluent.

When pyrolysis effluent leaves the reactor vessel, rapid quenching of reactions requires close-coupling of a cooling medium to the effluent outlet. Conventionally, super high pressure (SHP) steam generators are used to cool the effluent and recover heat for driving compression equipment. Using a common $CO_2$ loop for driving compression equipment, however, eliminates the need for an SHP steam system.

Instead, in various aspects the effluent is cooled by pyrolysis reactor feed effluent heat exchange. By eliminating atmospheric pressure heat exchange, and preheating feed with pressurized effluent, a desired amount of heat exchange can be performed in reduced area and volume, thus further reducing capital costs. Still additional heat integration can be achieved by cooling the working fluid leaving the combustion furnace by heat exchange with cold working fluid after water separation from the working fluid. Yet additional cooling needed for the overall process can be performed by generating dilution steam for cracking. Still further additional heating can be supplied at moderate temperature through integration with the hot $CO_2$ loop or potentially medium pressure steam condensation depending on economic optimization.

While a power cycle based on the Allam cycle can be provided with a single loop and power generator, steam cracking units typically include multiple compressors for cracked gas compression (CGC) and refrigeration compression as well as multiple parallel furnaces supplying cracked gas. In various aspects, the working fluid loop for an olefins production plant can include a plurality of combustor/turbine paths for compression drivers and a plurality of combustor/pyrolysis reactor paths. As an example, in one configuration, up to 3 parallel high pressure combustor/turbine paths for 3 compression drivers can be included in a working fluid loop along with 5 to 8 parallel low pressure combustor/pyrolysis reactor paths. This can provide the benefit, for example, of allowing a single reactor to undergo maintenance while the rest of the plant remains online.

The overall systems and methods can provide steam cracking of a feed for olefin production with an overall efficiency similar to existing state of the art steam crackers (>90%). In addition, the additional facilities for a compressor resemble those of a cracked gas compressor, of a size and duty familiar to ethylene plant operations. The capital cost addition of these additional facilities is lower than the cost of an amine unit for $CO_2$ removal from a dilute flue gas.

General Steam Cracker Operation

In a steam cracking process with a hydrocarbon feed (such as a feed substantially composed of ethane), the hydrocarbon feed is preheated, mixed with dilution steam, and then further preheated to a temperature at which significant thermal cracking is about to commence. For an ethane steam cracker, a feed including 50 vol % or more ethane can be used, or 70 vol % or more, or 90 vol % or more, such as up to having a feed substantially composed of ethane (i.e., more than 99 vol % ethane and up to 100%). In other aspects, any convenient type of feed can be used, including gas phase feeds (primarily composed of $C_{4-}$ hydrocarbons), liquid phase feeds, or a combination thereof. Examples of suitable feeds can include whole and partial crudes, naphtha boiling feeds, distillate boiling range feeds, resid boiling range feeds (atmospheric or vacuum), or combinations thereof. Additionally or alternately, a suitable feed can have a T10 distillation point of 100° C. or more, or 200° C. or more, or 300° C. or more, or 400° C. or more, and/or a suitable feed can have a T95 distillation point of 450° C. or less, or 400° C. or less, or 300° C. or less, or 200° C. or less. It is noted that the feed for pyrolysis (such as steam cracking) can be fractionated to remove a bottoms portion prior to performing pyrolysis, so that the feed entering the pyrolysis reactor has a T95 distillation point of 450° C. or less. The distillation boiling range of a feed can be determined, for example, according to ASTM D2887. If for some reason ASTM D2887 is not suitable, ASTM D7169 can be used instead.

The preheated feed and dilution steam can be passed to the radiant coil of a reactor where thermal cracking to produce olefins occurs. In the radiant or cracking zone of a steam cracking furnace that is operated at a conventional coil outlet pressure of ~150 kPa-g or less, the feed and dilution steam mixture is rapidly heated to high temperatures, such as roughly 1100° F.-1500° F. (~590° C.-~815° C.), to produce the desired product range. During such conventional operation, the residence time of the feed in the radiant or cracking zone can be quite low, such as roughly 0.1 seconds to 0.3 seconds.

Immediately following the radiant zone the mixture is rapidly cooled to quench the thermal cracking reactions. In various aspects, the cooling to quench the thermal cracking reactions can be performed in part by heat exchange with the input feed to the furnace tubes.

Representative Process Gas Compressor

In the compressor stage, the process gas is typically compressed to pressure in the range of from 20 bar (2000 kPa) to 40 bar (4000 kPa) in a centrifugal compressor powered by shaft power. Typically, the process gas compressor includes at least four sections, with each section in sequence providing an increase in pressure over its preceding sections. Cooling is typically employed between the sections, e.g., to prevent compressor damage, to prevent fouling resulting from diolefin polymerization, and to facilitate separation of process gas constituents. The invention is compatible with conventional process gas compressors, but the invention is not limited thereto.

EXAMPLE

This prophetic example is provided to illustrate the operation of a commercial scale steam cracker process train where one or more pressurized pyrolysis environments and one or more turbines share a $CO_2$-containing working fluid.

The capacity per pyrolysis reactor is selected to provide a practical shell diameter as well as a prudently-sized portion of the steam cracking plant flow to allow for maintenance of one reactor (as in for cracking tube replacement) without affecting overall steam cracker throughput. Based on typical configuration with pyrolysis furnaces, this results in about 7-8 reactors with 250-300 kTA of ethylene capacity per reactor for a world-scale 1800 kTA unit based on ethane. A reactor with approximately 160 U-tubes can provide this capacity. Based on tube pitch required from mean beam length calculations, this results in roughly 3 m-4.5 m diameter per reactor outside of refractory. To manage the corresponding process train for compressing and separating the process gas, up to three turbines can be used.

The furnace tubes can correspond to U-shaped tubes with an outer diameter of roughly 115 mm Based on the elevated pressure of operation, a triangular tube pitch can be set to 1.7-3.0 times the outer diameter to give same radiative efficiency as much larger firebox operated at a conventional 1.0 bar of total pressure (0.3 bar combined partial pressure of $CO_2$ and $H_2O$), with much reduced plot space and capital cost.

In this example, the pressurized pyrolysis environment can be operated at 13 bar (~1300 kPa-a) operating pressure. By using a working fluid that contains substantially only $CO_2$ and $H_2O$ (and therefore substantially no non-radiating $N_2$ in the working fluid), the radiative efficiency per unit volume is 40-45 times that of a conventional pyrolysis environment. Therefore, the mean beam length can be reduced to ~1/40 or 1/45 of the state of a conventional system, reducing plot space requirements.

As an example, the Furnace Calculation formulas from *Process Heat Transfer*, D. Q. Kern, Tata McGraw-Hill, 1997, page 691, can be used to calculate a suitable beam length.

The beam length for radiant heat transfer is defined as:

$L$ (ft)=⅔*(Length*Width*Height)$^{0.333}$ for fireboxes with dimensional ratios of 1×2×3. Based on this formula, $L$ (ft)=0.4*(Tube CL–CL distance in inches)–0.567*(Tube OD in inches) for tightly-packed banks of tubes as in convection sections or in pressurized radiant/convection heat transfer zones like those proposed herein.

Using the increased pressure and concentration of radiating flue gas, the beam length can be reduced to an unexpected degree, greatly reducing plot space and capital equipment costs.

In addition, by close-coupling tubes and providing a modest flue gas velocity powered by the internal pressure, additional heat transfer efficiency can be afforded through convection for further capital savings.

As an example of using this type of configuration, a process cycle similar to the cycle shown in FIG. 2 can be used. The fuel and oxygen input 610 can correspond to 90 tons per hour. This fuel is added to roughly 3300 tons per hour of substantially pure $CO_2$ working fluid from the prior process cycle. The combined fuel and working fluid can be at a pressure of roughly 20,000 kPa-a (~20 MPa-a). The roughly 3400 tons per hour of working fluid and fuel is distributed between three combustors for three turbines to provide power for the process gas compressor and refrigeration units for processing the pyrolysis effluent. After powering the turbine, the pressure of the 3400 tons per hour of working fluid is reduced to roughly 3000 kPa-a. An additional 90 tons per hour of fuel and oxygen is added to the 3400 tons per hour of low pressure working fluid. This roughly 3500 tons per hour of fuel and low pressure working fluid is passed into seven combustors that are each close coupled with a corresponding pressurized pyrolysis reactor. After providing heat for the pyrolysis environment, the pressure of the 3500 tons per hour of working fluid can be further reduced to roughly 1300 kPa-a. The depressurized working fluid can then be heat exchanged with the substantially pure $CO_2$ working fluid used at the start of this process cycle. After heat exchange, roughly 100 tons per hour of water can be removed from the working fluid in a series of cooling and compression steps. It is noted that if tail gas from the steam cracking process is used rather than natural gas as the fuel, the amount of water removed at this point can be larger. After water removal, the substantially pure $CO_2$ working fluid can be at a pressure of roughly 8000 kPa-a. At this point, roughly 90 tons per hour of $CO_2$ can be removed, to maintain a constant level of working fluid in the loop. It is noted that if tail gas from the steam cracking process is used rather than natural gas as the fuel, the amount of $CO_2$ removed can be less. The remaining working fluid can then be compressed up to the desired pressure of roughly 20 MPa-a for the combustors associated with the turbines.

This type of configuration can be used to perform steam cracking on a feed containing 100 tons per hour of ethane along with 30 tons per hour of diluent steam. This feed can be passed into the furnace tubes for pyrolysis. The resulting pyrolysis effluent can include a mixture of hydrocarbons and hydrogen, including more than 50 wt % of ethylene.

Additional Configuration Example—Integration with Safety Relief Devices

Cracking furnaces are typically equipped with emergency shutdown systems (trip systems) that automatically take the furnace to a safe condition when a potentially unsafe condition is detected on the furnace. Historically these trip systems shut at least a portion of the input feed to the steam cracker furnace tubes, with supplemental steam used as needed to maintain a sufficient temperature to prevent fracture over the coke layer inside the tubes.

Ethylene plants are always equipped with a flare system to safely combust excess gas that can be generated, for example, by the shutdown of the process gas compressor. In the case of a process gas compressor shutdown, gas continues to enter the quench tower from the furnaces and the quench tower pressure rises. At a pre-set pressure, relief valves on the quench tower will open to the flare system to prevent damage to the quench tower from excessively high pressures.

Historically ethylene plants used elevated flares, where large volumes of gas were combusted in a single, large flare-tip. Flare-tips were designed to facilitate the mixing of air with the flare-gas, but the volume and composition of gas flared following a process gas compressor trip would often lead to the generation of significant smoke at the flare-tip. Addition of steam to the flare gas proved effective at suppressing flare tip smoking, but the cooling/dilution effect of the steam was found to reduce the hydrocarbon combustion efficiency. Thus instead of flare gas being completely combusted to $CO_2$ and $H_2O$, some incompletely combusted hydrocarbons were released to the atmosphere. These compounds are considered air pollutants and can contribute to the formation of photochemical smog.

To achieve smokeless flaring while also achieving high hydrocarbon destruction efficiency, modern ethylene plants are often equipped with a so-called "ground flare". A ground flare comprises a large number of small burner tips that are each designed to inspirate sufficient air to burn smokelessly. A ground flare covers a significant area of real-estate, and is typically equipped with radiation barrier walls around its perimeter.

Ground flares rely on the flare gas having a sufficiently high heating value, often measured in Btu/SCF (British Thermal Units [energy] per Standard Cubic Feet [volume]), to assure full combustion of the contained hydrocarbons and also to allow each individual burner tip to light from the flame on the adjacent burner tip (so-called "cross-lighting"). A common requirement is to have a flare gas heating value of no lower than 800 Btu/SCF (~30 MJ/m³). Unfortunately, during a steam partial trip where the process gas compressor is also shut down, the steam used to protect the furnace tubes is added to the flare gas. This additional steam from the process gas compressor can significantly lower the heating value of the flare gas. In order to maintain a target heating value for the flare gas, substantial amounts of additional feed and/or fuel have to be added to the flare gas, resulting in substantial amounts of additional $CO_2$ emissions.

In some aspects, the various amounts and pressures of the $CO_2$ used as the working fluid in the Allam cycle can allow for recovery of large volumes of flare gas into the loop used for the Allam cycle, rather than merely uneconomic flaring. In addition to reducing costs, this can also reduce, minimize, or avoid environmental emissions.

As described above, FIG. 2 shows an example of an Allam cycle for using a common $CO_2$-containing working fluid for both a) a turbine for providing shaft power to the pyrolysis effluent processing train and b) for a low pressure combustor to provide heat to the pyrolysis furnace. When a "trip" event occurs, the feed to the pyrolysis tubes is typically reduced or minimized, so that processing of the pyrolysis effluent is not required. This means that the need for shaft power for the process gas compressor (and/or other compressors and/or cooling stages for handling the pyrolysis effluent) is reduced or minimized. Therefore, the $CO_2$ working fluid loop can potentially be used for other purposes during a trip event.

In some aspects, during a trip event, instead of venting the gas from the process gas compressor and/or quench tower and/or other locations as flare gas, the vented gas can be redirected into the $CO_2$ working fluid loop. For example, as shown in FIG. 2, the $CO_2$ working fluid in the working fluid loop has a pressure of roughly 30 MPa-a prior to being used to drive the turbine to provide shaft power. Instead of driving a turbine, this pressurized $CO_2$ can be used to educt large volumes of flare gas, to form a combined working fluid and flare gas flow with a pressure that is suitable to be passed into the low pressure combustor. This can be achieved by combining the pressurized $CO_2$ working fluid and flare gas so that the mass flow rate of pressurized $CO_2$ working fluid is roughly 4 times to 10 times as great (or 5 times to 7 times as great) as the mass flow rate of flare gas. This can result in a combined working fluid and flare gas flow with a pressure of roughly 1.0 MPa-a to 4.0 MPa-a, which is suitable for introduction into the low pressure combustor.

In this type of configuration, the limit of flare gas consumed corresponds to the tolerable amount of firing in the reactors, which is similar to the amount of flared effluent produced during a conventional process gas compressor trip scenario. Therefore, the flare gas output can be ratably controlled by the reactor feed rate, which is heated by recycled flare gas. Typically in these situations, to park furnaces or reactors in a safe state and minimize flaring, hydrocarbon feed is replaced with steam, minimizing hydrocarbon in the unit and keeping reactors warm. However, major flaring scenarios like these in a conventional or ground flare system are governed by challenging standards for maintaining combustion efficiency in the flares. These standards are necessary to prevent hydrocarbon release to the environment, but also limit operating flexibility and upset response by limiting steam in furnace effluent to the flare. By educting flare material into the low pressure combustor, and keeping flare material inside the loop, emissions can be combusted more efficiently at higher pressure even at higher steam rates. Further, destruction efficiency is not as important as in direct atmospheric discharge, as left over uncombusted material will be recycled in the loop until fully combusted or discharged as a trace component of $CO_2$ streams.

All patents, test procedures, and other documents cited herein, including priority documents, are fully incorporated by reference to the extent such disclosure is not inconsistent. It is not intended that the scope of the claims appended hereto be limited to the descriptions set forth herein but rather that the claims be construed as encompassing all patentable features which reside herein, including all features which would be treated as equivalents thereof by those skilled in the relevant art. When lower and upper limits are specified, ranges from any lower limit to any upper limit are expressly within the scope of the invention. The term "comprising" is synonymous with the term "including". When a composition, an element or a group of components is preceded with the transitional phrase "comprising", the same composition or group of components is within transitional phrases "consisting essentially of," "consisting of," "selected from the group of consisting of," or "is" preceding the recitation of the composition, component, or components, and vice versa. Pressure values are absolute (bar, kPa, psi, or psia) unless expressly indicated as gauge (barg, kPag, psig).

The invention claimed is:

1. A process for performing pyrolysis, comprising:

separating from air at least an oxygen-containing stream, the oxygen-containing stream comprising 90 vol. % or more $O_2$;

combusting a first fuel with a first portion of the oxygen-containing stream in the presence of at least a portion of a recycle stream at a pressure of 10 MPa-a or more to produce a heated working fluid, the recycle stream comprising 80 vol. % or more $CO_2$;

operating a turbine using the heated working fluid to produce power and an intermediate working fluid comprising at least $CO_2$ and $H_2O$;

combusting a second fuel with a second portion of the oxygen-containing stream in the presence of the intermediate working fluid to form a heated intermediate working fluid;

exposing the heated intermediate working fluid to a plurality of furnace tubes in a pressurized pyrolysis environment to transfer heat to the plurality of furnace tubes and produce a depressurized working fluid comprising a pressure of 800 kPa-a to 3000 kPa-a;

pyrolyzing at least a portion of a hydrocarbon-containing feed in the plurality of furnace tubes to form a pyrolysis effluent comprising at least a process gas comprising ethylene;

transferring at least part of the produced power a) to a process gas compressor to compress the process gas, b) to a refrigeration compressor to cool the process gas, c) to a refrigeration compressor to cool the depressurized working fluid in a cooling step in a series of cooling and compressing steps, or d) a combination of two or more of a), b) and c);

performing the series of cooling and compressing steps on the depressurized working fluid to form a water stream and a $CO_2$-containing stream, the $CO_2$ in the depressurized working fluid and the $CO_2$-containing stream being in a single phase during the series of cooling and compressing steps; and compressing at least a portion of the $CO_2$-containing stream to form a compressed $CO_2$-containing stream, the recycle stream comprising at least a first portion of the compressed $CO_2$-containing stream.

2. The process of claim 1, wherein the depressurized working fluid comprises 90 vol. % or more of $CO_2$ and $H_2O$.

3. The process of claim 1, wherein compressing at least a portion of the process gas using the produced power comprises direct power transfer of the produced power, indirect power transfer of the produced power, or a combination thereof.

4. The process of claim 1, wherein at least one of the first fuel and the second fuel comprises a tail gas formed from the compressed process gas.

5. The process of claim 1, wherein the at least one of the first fuel and the second fuel comprises one or more of (i) natural gas, (ii) hydrocarbon in the natural gas, (iii) hydrocarbon separated from the natural gas and/or derived from the natural gas, (iv) natural gas condensate, (v) hydrocarbon in the natural gas condensate, (vi) hydrocarbon separated from the natural gas condensate and/or derived from the natural gas condensate, (vii) crude oil, (viii) hydrocarbon in the crude oil, (viii) hydrocarbon separated from the crude oil and or derived from the crude oil, and (ix) molecular hydrogen.

6. The process of claim 1, wherein the feed comprises >10 wt. % $C_{2+}$ hydrocarbon.

7. The process of claim 1, wherein the compressed $CO_2$-containing stream comprises a pressure of 10 MPa-a or more.

8. The process of claim 1, wherein the intermediate working fluid comprises a pressure of 3000 kPa-a to 6000 kPa-a.

9. The process of claim 1, further comprising transferring at least a second portion of the produced power to a compressor for i) performing the compressing in the series of cooling and compressing steps, ii) performing the compressing of the $CO_2$-containing stream, or iii) a combination of i) and ii).

10. The process of claim 1, wherein the pyrolyzing of the feed comprises pyrolyzing the feed under steam cracking conditions.

11. The process of claim 1, wherein the recycle stream comprises 95 vol % or more $CO_2$.

12. The method of claim 1, further comprising performing heat exchange between the at least a portion of the depressurized working fluid and at least a portion of the recycle stream.

13. The method of claim 1, further comprising performing heat exchange between at least a portion of the pyrolysis effluent and at least a portion of the feed.

14. The process of claim 1, wherein at least a portion of the water stream is (i) fed into the pyrolyzing step to mix with the hydrocarbon-containing feed; (ii) heated to generate steam; (iii) used as an indirect cooling medium; (iv) used as a quenching medium; and (iv) fed into a hydrocarbon-containing stream as a diluent.

15. The process of claim 1, further comprising:

recovering an ethylene stream from the process gas;

contacting at least a portion of the ethylene stream with at least a portion of the oxygen-containing stream to produce an oxidized stream; and producing a monoethylene glycol product from the oxidized stream.

16. The process of claim 15, wherein the oxidized stream comprises ethylene oxide, and the step of producing the monoethylene glycol product comprises contacting the ethylene oxide with the $CO_2$ sourced from the compressed $CO_2$ stream and/or the $CO_2$-containing stream.

17. The process of claim 1, further comprising at least one of the following:

supplying a portion of the compressed $CO_2$ stream to a storage;

conducting away a portion of the compressed $CO_2$ stream in a pipeline;

using a portion of the compressed $CO_2$ stream to extract a hydrocarbon source material, and deriving at least a portion of the hydrocarbon-containing feed from the hydrocarbon source material.

* * * * *